United States Patent [19]
Natori

[11] Patent Number: 5,055,392
[45] Date of Patent: Oct. 8, 1991

[54] CLONING OF DNA ENCODING TRANSCRIPTION FACTOR S-11

[75] Inventor: Shunji Natori, Tone, Japan

[73] Assignee: Sanwa Kagaku Kenkyusho Co., Ltd., Nagoya, Japan

[21] Appl. No.: 246,244

[22] Filed: Sep. 19, 1988

[30] Foreign Application Priority Data

Sep. 29, 1987 [JP] Japan ................... 62-242817

[51] Int. Cl.$^5$ .................... C12N 15/00; C12N 15/12; C12N 15/63
[52] U.S. Cl. .................... 435/6; 435/172.3; 435/320.1; 536/27
[58] Field of Search ............ 536/27; 435/320,6, 172.3

[56] References Cited

PUBLICATIONS

Reinberg & Roeder, J. Biol. Chem., vol. 262, pp. 3331–3337 (1987).
Suggs et al, PNAS, vol. 78, pp. 6613–6617 (1981).

Primary Examiner—Richard A. Schwartz
Assistant Examiner—S. L. Nolan
Attorney, Agent, or Firm—Armstrong, Nikaido, Marmelstein, Kubovcik & Murray

[57] ABSTRACT

A cloned single-strand DNA encoding amino acid sequence for a eukaryotic transcription factor S-11 is disclosed together with, a cloned double-strand DNA consisting of the single-strand DNA and its complementary single-strand DNA, a DNA fragment of the single- or double-strand DNA, a process for the preparation thereof, a plasmid, in which the double-strand DNA or its fragment is inserted, and a diagnosis of viral diseases and cancers.

5 Claims, 8 Drawing Sheets

E: EcoRI   D: DraI
X: XhoI    Pv: PvuII
P: PstI    B: BamHI
S: SacI    H: HindIII

FIG. 2

Peak I :
```
        1               5
        Asp Thr Tyr Val Ser Ser Phe Pro Arg
```

Peak II :
```
        1                          10
        Thr Gly Asp Asp Tyr Val Ala Ile Gly Ala Asp Glu Glu Leu Gly
                                A
        3'- CTA CTA ATA CAG CG -5'       3'- CTA CTC CTC CTC AA -5'
             G   G   G   C                            G  T   T   G
                         T
```

FIG. 4 (1/5)

```
▶pSII-1                    ▶pSII-3
    1              20              40              60              80
    GAATTCGGACACAGCCGACGGGAAGCGAGAGAAGCTGCGGACAAGCCGGAACGCGCTGGCCGAGGCCTTCCGGAGCCATG
                                                                                 Met   1
                                                              (1)
                                                              pSII-2 ▶GA
    100             120             140             160
    GAGGACGAGGTGGTTCGCATTGCCAAGAAGATGGACAAAAGAATGCGGTGGCGCATTGGATTGCTGAAAGAG
    GluAspGluValValArgIleAlaLysLysMetAspLysMetValGlnLysLysAsnAlaGlyAlaAlaLeuAspLeuLeuLysGlu  30
```

FIG. 4 (2/5)

```
         180              200              220              240              260
CTTAAGAATATTCCATGACCCTAGAATTGCTACAGTCCACAGAATTGGAATGTCTGTCAATGCCCTTCGCAAGCAGAGCACAGAT     59
LeuLysAsnIleProMetThrLeuGluLeuLeuSerThrArgIleGlyMetSerValAsnAlaLeuArgLysGlnSerThrAsp 280              300              320              340
GAAGAAGTCACCTCTCTAGCCAAGTCTCTCATCAAATCCTGGAAAAAATTATTAGATGGACCATCAACTGATAAAGACCCTGAAGAA     88
GluGluValThrSerLeuAlaLysSerLeuIleLysSerTrpLysLysLeuLeuAspGlyProSerThrAspLysAspProGluGlu 360              380              400              420
AAGAAAAAGAGCCTGCAATTTCATCACAGAATAGCCCTGAAGCAAGAAGAGAAAGTAGTTCCAGCAATGTAAGCAGCAGAAAG       117
LysLysLysGluProGlnPheHisHisArgIleAlaLeuLysGlnGluGluLysValValProAlaMet***

440              460              480              500              520
GATGAGACAAATGCTCGAGATACATATGTTTCATCTTTCCTCGCGCACCAAGCACTTCTGATTCTGTGCGATTAAAATGTAGGGAG   146
AspGluThrAsnAlaArgAspThrTyrValSerSerPheProArgAlaProSerThrSerAspSerValArgLeuLysCysArgGlu 540              560              580              600
ATGCTTGCTGCAGCTCTTCGGACAGGAGATGATTATGTTGCAATTGGAGCTGATGAAGAAGAACTGGGATCTCAGATTGAGGAAGCT   175
MetLeuAlaAlaAlaLeuArgThrGlyAspAspTyrValAlaIleGlyAlaAspGluGluGluLeuGlySerGlnIleGluGluAla 620              640              660              680
ATATCAAGAAATAAGGAATACAGAACATGAAATACAAAAACAGAGTACGAAGTAGGATATCAATCTTAAAGATGCAAAGAATCCA   204
IleTyrGlnIleArgAsnThrAspMetLysTyrLysAsnArgValArgSerArgIleSerAsnLeuLysAspAlaLysAsnPro
```

FIG. 4 (3/5)

```
700                720                740                760                780
AATTTAAGGAAAAAATGTGCTGTGTGGGAATATTCCCTCCTGATCTATTGCTAGAATGACAGCAGAGGAAATGGCTAGTGATGAGCTC
AsnLeuArgLysAsnValLeuCysGlyAsnIleProProAspLeuPheAlaArgMetThrAlaGluMetAlaSerAspGluLeu       233
              pSⅡ-1

800                820                840                860
AAAGAGATGAGGAGAAAAACCTGACCAAAGAAGCCATCAGGGACCATCAGATGGCCAAGACTGGTGGACCCAGACTGACTTGTTCACT
LysGluMetArgLysAsnLeuThrLysGluAlaIleArgAspHisGlnMetAlaLysThrGlyGlyThrGlnThrAspLeuPheThr    262

880                900                920                940
TGTGGCAAATGTAAAAAGAAGAACTGCACTTATACACAGGTGCAAACTCGTAGTGCTGATGAACCAATGACAACATTTGTTGTA
CysGlyLysCysLysLysAsnCysThrTyrThrGlnValGlnThrArgSerAlaAspGluProMetThrThrPheValVal          290

960                980                1000               1020               1040
TGTAATGAATGTGGAAATCGGTGGAAGTTCTGTTGAGTTTGGAAGAATTGGCAAAGTATCTGGACCATTAAGAAAAACTTAATTTTG
CysAsnGluCysGlyAsnArgTrpLysPheCys***                                                       301

1060               1080               1100               1120
TTAATTAGCTTTAAAATTAAGCCAGGCAACTCGTTTCCTTGCAAGTGAAATTTGTAAACAACATACATCTCATGGTTGGTCTTTGT 1140               1160               1180               1200
TGTTCACCTGACAGTCTGTCTTAAATGCCTTCTGTGGTCTCAGATCAGCTGGGAGACCATAAAATAATGATATAATGTGTTGCTTTG
                                                                              pSⅡ-3
```

FIG. 4 (4/5)

```
1220            1240                1260                1280                1300
TTTTCTCTTTCATAAGTTGATGTTGCATTTTATTAAATATTAACTTTTATAGCCTAGAACACAAAAATTTTGTTGATCTGTTAATGCA 1320                1340                1360                1380
TAAAGATAAATTGCTTTTCTCATTGGTATGTACCTAAACATGTTAAAAAGGAAAAAGGCATAATATAAATTTTAGAGTTACCAAATGTAGT 1400            1420                1440                1460                1480
GTGTATTCCAATAGTATGTGGCCAGCTTATCAAAGTTGTGCACACAATTTGAACTAGCATATTACTTACTCTTAATTACTGTGCTCACA 1500                1520                1540                1560
AAGCCTCGGATCCTCTTGGATCTCTGTGACTAACCACAGTGATCATTTCTTTTATTTCTCATACATATAATACCATTTTTAA 1580            1600                1620                1640                1660
TAGATTTTACTCTGAAAACGGACTTGGTTTATTTTATTTGACTTTGTGCTATATTTTAGTTTTATAGAACTCTGTTATAATTCCTAAGC 1680                1700                1720                1740
TTTTCATAAAGCCCCACCACAGGTATACTTCTGATGAATTGTCCCCAATAGGAAGACATGCTATGAAGAAAATGTTAGTATCTTAGTAGAC 1760            1780                1800                1820                1840
TTCCTGGAGGCAGCATGACTGTACTTGCACTTGGAAACCTACTGACCAAGGATTAAGCCTGAGAACTGTGTAAATCATTAAGCTATGCTC 1860                1880                1900                1920
TTTGTGTATGGAGGTTGCAAAAAAAGGCACCTCCTTTAGACTGAATCTTTTGTGCTGAAATTTTTCTTACATGATGATGTCAACCCAGCT
```

FIG. 4 (5/5)

```
1940                    1960                    1980                    2000                    2020
GAAATGTAGGCTGTAGCAAATAGTTTTACAAAACATATTTCACAATTAAGTTTTACTTTTTAAATGTCCCACTTGTTTTGCTAGTAAT 2040                    2060                    2080                    2100
AAGCAGTGGTTTCACATCGTCTCTTCCTGAGAGAGATGTGTAATGCATATAGTAAAGGCCACTTTTATAAATTAAGTGCTTCTGCCTGTG 2120                    2140                    2160                    2180                    2200
TTCAGACTCCTGTGTAAAAACCGTTGCACAAGCTTGCACTCTTCTATGCTCTGCTTTGTAGACCGTTTGTCATAACATGGAAAACAATA 2220                    2240                    2260                    2280
TGTCCATGTTAAAAGGATTGGTCTGCCGGGGCGTGGTGGCCCACACCCTTTAATCCCAGAACTCGGGAGGCAGAGGCAGGGGATTCTGAG 2300                    2320                    2340                    2360                    2380
TTTGAGGCCAGCCTGGTCTACAGAGTGAGTTCCAGGACAGCCAGGGCTATACAGAGAAACCCTGTCTCAACCCCCTCCCCCCCCCAAAA 2400                    2420                    2440                    2460
AAAAGATTGGTCCATGGATAATTTCTGTCACTTTAAAAATAAAGTACAGTTTGAAAGAATTAGTTTAAAAGTAATAAGGTTAAAATAGTC 2480                    2500                    2520       2535
CCACTTTAAGTGATCCATTTAAAATTTGTAAATCAATAAAGTTTTTTGTTGTTAAAC - - - poly A
pS II - 2
```

CLONING OF DNA ENCODING TRANSCRIPTION FACTOR S-11

BACKGROUND OF THE INVENTION

1. Field of the Invention

The present invention relates to a cloned single-strand DNA encoding amino acid sequence for a eukaryotic transcription factor S-II, a cloned double-strand DNA consisting of the single-strand DNA and its complementary single-strand DNA, a DNA fragment of the single- or double-strand DNA, a process for the preparation thereof, a plasmid, in which the double-strand DNA or its fragment is inserted, and a diagnostic reagent for the detection of diseases and more particularly viral diseases and cancers.

2. Related Arts

A transcription factor S-II is a protein, which was first separated and isolated by the present inventor from an Ehrlich ascites tumor cell and which shows a promotion of accuracy and efficiency of transcription through an eukaryotic RNA polymerase II ["Mol. Cell. Biochem." Vol. 46, pages 173-187 (1982)]. Thereafter, the same transcription factor has also been isolated from a bovine thymus suggesting that the substance is the factor commonly presents in eukaryotic cells ["J. Biol. Chem." Vol. 262, pages 5227-5232 (1987)].

In connection with a diagnosis of viral diseases and cancers, and more particularly the acquired immune deficiency syndrome (AIDS) among the virus diseases, a diagnosis using an antibody to HIV has generally been employed. Retroviruses such as HIV has been known to replicate using host RNA polymerase II. Besides RNA polymerase II, it is widely acknowledged that various cellular factors play a roll in eukaryotic transcriptional controls.

It has been apparent, as referred to, that the transcription factor S-II is present in eukaryotic cells, but its structure has not been elucidated. According to the prior arts, further, the transcription factor S-II has been prepared by separation and extraction from the cells and thus the preparation thereof in large amount was difficult.

While, various methods have been proposed to use a certain antibody for making a diagnosis of viral diseases and cancers and, more particularly, in the diagnosis of AIDS, such an antibody diagnosis has is not always conclusive and there is no subsidiary diagnostic method, which sometimes makes impossible rather than difficult an exact diagnosis, such as when an antigen-antibody reaction shows a false positive.

SUMMARY OF THE INVENTION

A basic object of the invention, therefore, is to develop a process for large scale preparation of the transcription factor S-II by utilizing so-called "Bio-Technology" and a diagnostic method for viral diseases and cancers, which utilizes a gene of the transcription factor S-II.

A primary object of the invention, therefore, is to provide a cloned DNA comprising the transcription factor S-II and a fragment of the DNA to allow a large scale preparation of the transcription factor S-II by use of a recombinant DNA methods.

An additional object of the invention is to provide the diagnostic method for AIDS and other viral diseases and cancers, which employs a cloned DNA comprising the transcription factor S-II or the DNA fragment, so as to increase diagnostic accuracy for the diseases by combining the method with any one of known conventional methods.

The present inventor has carefully and energetically studied and investigated the problem to finally gain success in the cloning of DNA in the region containing the transcription factor S-II, to determine its structure and to find out that in cancer cells and cells infected by virus, and more particularly cells infected with HIV, an expression of mRNA for transcription factor S-II becomes augmentative, for instance 10 fold or more, in comparison with that in normal cells.

DETAILED DESCRIPTION OF THE INVENTION

According to the invention, the primary object can be attained using isolating cloned single-strand DNA comprising about 2500 nucleotides which contains a nucleotide sequence encoding an amino acid sequence for the eukaryotic transcription factor S-II, or a cloned double-strand DNA consisting of the single-strand DNA and its complementary single-strand DNA.

According to a process of the invention, the cloned single- or double-strand DNA can be prepared by extraction and purification of poly(A)RNA from Ehrlich ascites tumor cells, constructing a cDNA library with use of the poly(A)RNA and a vector DNA to carry out a transformation of *Escherichia coli* (*E. coli*), while, previously synthesizing a mixture of 32 dotriacontamers, each consisting of 14 oligodeoxyribonucleotides of the formula

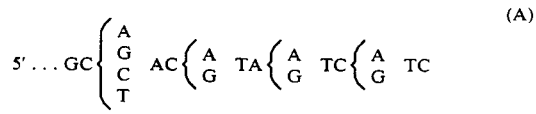 (A)

which is complementary to mRNA corresponding to

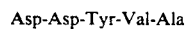

of 3rd to 7th amino acids from N-terminal in known amino acid sequence in peak II for a fragment which is obtained by cleaving with trypsin the known transcription factor S-II obtained from Ehrlich ascites tumor cells and a mixture of 32 dotriacontamers, each consisting of 14 oligodeoxyribonucleotides of the formula

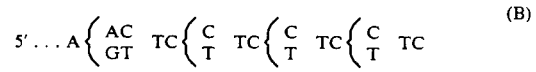 (B)

which is complementary to mRNA corresponding to

of 11th to 15th amino acids from N-terminal in the known amino acid sequence, labelling each synthesized oligodeoxyribonucleotides shown by said formulae (A) and (B) at its N-terminus, screening said transformed *E. coli* by hybridization using said labelled oligodeoxyribonucleotides as probes to obtain a cloned double-strand DNA as positive clone which hybridizes to both of the probe groups, and if necessary, separating the double-strand DNA into single-strand DNA, in a conventional manner.

The ground that the 3rd to 7th amino acids from N-terminal in amino acid sequence of the known polypeptide for transcription factor S-II are selected for the oligodeoxyribonucleotides (A) as one of probe groups and that the 11th to 15th amino acids from N-terminal amino acid sequence of the known polypeptide for transcription factor S-II are selected for the oligodeoxyribonucleotides (B) as the other probe group lies in minimizing the kinds of oligodeoxyribonucleotides to be synthesized for responding to the pentapeptide. In the screening of the transformed cells (*E. coli*), there is no difference in result, even if the hybridization with the oligodeoxyribonucleotides (A) is carried out prior to that with the other oligodeoxyribonucleotides (B), or vice versa. The cloned single-strand DNA can be prepared by separating the cloned double-strand DNA with use of a method known per se, for instance thermally treating at 90° C. for about 3 minutes and then cooling the same with use of an ice bath.

The transcription factor S-II according to the invention has about 900 nucleotides of the following nucleotide sequence or any other nucleotide sequence producing the same protein, taking into consideration the redundancy of the genetic code.

5'... ATG GAG GAC GAG GTG GTT CGC ATT GCC

AAG AAG ATG GAC AAA ATG GTG CAG AAA AAG

AAT GCG GCT GGC GCA TTG GAT TTG CTG AAA GAG

CTT AAG AAT ATT CCC ATG ACC CTA GAA TTG CTA

CAG TCC ACA AGA ATT GGA ATG TCT GTC AAT GCC

CTT CGC AAG CAC AGC ACA GAT GAA GAA GTC ACC

TCT CTA GCC AAG TCT CTC ATC AAA TCC TGG AAA

AAA TTA TTA GAT GGA CCA TCA ACT GAT AAA GAC

CCT GAA GAA AAG AAA AAA GAG CCT GCA ATT TCA

TCA CAG AAT AGC CCT GAA GCA AGA GAA GAA

AGT AGT TCC AGC AGC AAT GTA AGC AGC AGA

AAG GAT GAC ACA AAT GCT CGA GAT ACA TAT GTT

TCA TCT TTT CCT CGC GCA CCA AGC ACT TCT GAT

TCT GTG CGA TTA AAA TGT AGG GAC ATG CTT GCT

GCA GCT CTT CGC ACA GGA GAT GAT TAT GTT GCA

ATT GGA GCT GAT GAA GAA GAA CTG GGA TCT

CAG ATT GAG GAA GCT ATA TAT CAA GAA ATA AGG

AAT ACA GAC ATG AAA TAC AAA AAC AGA GTA CGA

ACT AGG ATA TCA AAT CTT AAA GAT GCA AAG AAT

CCA AAT TTA AGG AAA AAT GTG CTG TGT GGG AAT

ATT CCT CCT GAT CTA TTT GCT AGA ATG ACA GCA

GAG GAA ATG GCT AGT GAT GAG CTC AAA GAG

ATG AGG AAA AAC CTG ACC AAA GAA GCC ATC

AGG GAG CAT CAG ATG GCC AAG ACT GGT GGG

ACC CAG ACT GAC TTG TTC ACT TGT GGC AAA TGT

AAA AAG AAG AAC TGC ACT TAT ACA CAG GTG CAA

ACT CGT AGT GCT GAT GAA CCA ATG ACA ACA TTT

GTT GTA TGT AAT GAA TGT GGA AAT CGG TGG AAG

TCC TGT ... 3' wherein A, C, G and T are respectively an oligodeoxyribonucleotide having adenine, cytosine, guanine or thymine base and said sequence is given as that of each codon corresponding to a specified amino acid.

The term of —Nucleotide sequence same in producing the same protein— means a case of that even when the arrangement of nucleotides constituting codons, such as —TTA— and —CTG— are different but each of the codons designates same amino acid, according to the redundancy of the genetic code. Therefore, the term means all known or possible nucleotide sequences encoding the following amino acid sequence:

Met—Glu—Asp—Glu—Val—Val—Arg—Ile—Ala—Lys—Lys—

Met—Asp—Lys—Met—Val—Gln—Lys—Lys—Asn—Ala—Gly—

Ala—Ala—Leu—Asp—Leu—Leu—Lys—Glu—Leu—Lys—Asn—

Ile—Pro—Met—Thr—Leu—Glu—Leu—Leu—Gln—Ser—Thr—

Arg—Ile—Gly—Met—Ser—Val—Asn—Ala—Leu—Arg—Lys—

Gln—Ser—Thr—Asp—Glu—Glu—Val—Thr—Ser—Leu—Ala—

Lys—Ser—Leu—Ile—Lys—Ser—Trp—Lys—Lys—Leu—Leu—

Asp—Gly—Pro—Ser—Thr—Asp—Lys—Asp—Pro—Glu—Glu—

Lys—Lys—Lys—Glu—Pro—Ala—Ile—Ser—Ser—Gln—Asn—

Ser—Pro—Glu—Ala—Arg—Glu—Glu—Ser—Ser—Ser—Ser—

Ser—Asn—Val—Ser—Ser—Arg—Lys—Asp—Glu—Thr—Asn—

Ala—Arg—Asp—Thr—Tyr—Val—Ser—Ser—Phe—Pro—Arg—

Ala—Pro—Ser—Thr—Ser—Asp—Ser—Val—Arg—Leu—Lys—

Cys—Arg—Glu—Met—Leu—Ala—Ala—Ala—Leu—Arg—Thr—

Gly—Asp—Asp—Tyr—Val—Ala—Ile—Gly—Ala—Asp—Glu—

Glu—Glu—Leu—Gly—Ser—Gln—Ile—Glu—Glu—Ala—Ile—

Tyr—Gln—Glu—Ile—Arg—Asn—Thr—Asp—Met—Lys—Tyr—

Lys—Asn—Arg—Val—Arg—Ser—Arg—Ile—Ser—Asn—Leu—

Lys—Asp—Ala—Lys—Asn—Pro—Asn—Leu—Arg—Lys—Asn—

Val—Leu—Cys—Gly—Asn—Ile—Pro—Pro—Asp—Leu—Phe—

Ala—Arg—Met—Thr—Ala—Glu—Glu—Met—Ala—Ser—Asp—

Glu—Leu—Lys—Glu—Met—Arg—Lys—Asn—Leu—Thr—Lys—

Glu—Ala—Ile—Arg—Glu—His—Gln—Met—Ala—Lys—Thr—

Gly—Gly—Thr—Gln—Thr—Asp—Leu—Phe—Thr—Cys—Gly—

Lys—Cys—Lys—Lys—Lys—Asn—Cys—Thr—Tyr—Thr—Gln—

Val—Gln—Thr—Arg—Ser—Ala—Asp—Glu—Pro—Met—Thr—

Thr—Phe—Val—Val—Cys—Asn—Glu—Cys—Gly—Asn—Arg—

Trp—Lys—Phe—Cys

The cloned DNA having about 900 nucleotides can be obtained by treating the cloned DNA having about 2500 nucleotides with a suitable restriction enzyme(s), for instance EcoRI and PvuII, and shorter fragments can be prepared by treating the cloned DNA having about 2500 to 900 nucleotides with a suitable restriction enzyme(s). In case of that a desired fragment can not be obtained with the treatment by the restriction enzyme(s), a region(s) not obtaining with the cleaving technique may be synthesized with use of a DNA synthesizer and the resulting region is(are) joined to one or both ends of the fragment obtained through the enzyme treatment.

The cloned DNA having about 2500 nucleotides, or any fragment thereof can be inserted into a plasmid with a technique known per se, for instance taking out a plasmid from E. coli, purifying the plasmid, treating the plasmid with a restriction enzyme(s) to cleave the plasmid at the nucleotide position inherent in the enzyme, and ligating with a DNA ligase the cloned DNA to the cleavages of the cut plasmid to reconstruct a plasmid with the recombinant DNA.

If a microorganism or eukaryotic cell (L, CHO or the like) is transformed with the plasmid which contains the recombinant DNA according to the invention and cultivated the same, the transcription factor S-II or other biologically active substances can be produced in a large amount.

A diagnostic method for viral diseases and cancers according to the invention is characterized by labelling the cloned DNA having about 2500 nucleotides which include the nucleotide sequence encoding the amino acid sequence for the transcription factor S-II of Met—Glu—Asp—Glu—Val—Val—Arg—Ile—Ala—Lys—Lys—

Met—Asp—Lys—Met—Val—Gln—Lys—Lys—Asn—Ala—Gly—

Ala—Ala—Leu—Asp—Leu—Leu—Lys—Glu—Leu—Lys—Asn—

Ile—Pro—Met—Thr—Leu—Glu—Leu—Leu—Gln—Ser—Thr—

Arg—Ile—Gly—Met—Ser—Val—Asn—Ala—Leu—Arg—Lys—

Gln—Ser—Thr—Asp—Glu—Glu—Val—Thr—Ser—Leu—Ala—

Lys—Ser—Leu—Ile—Lys—Ser—Trp—Lys—Lys—Leu—Leu—

Asp—Gly—Pro—Ser—Thr—Asp—Lys—Asp—Pro—Glu—Glu—

Lys—Lys—Lys—Glu—Pro—Ala—Ile—Ser—Ser—Gln—Asn—

Ser—Pro—Glu—Ala—Arg—Glu—Glu—Ser—Ser—Ser—Ser—

Ser—Asn—Val—Ser—Ser—Arg—Lys—Asp—Glu—Thr—Asn—

Ala—Arg—Asp—Thr—Tyr—Val—Ser—Ser—Phe—Pro—Arg—

Ala—Pro—Ser—Thr—Ser—Asp—Ser—Val—Arg—Leu—Lys—

Cys—Arg—Glu—Met—Leu—Ala—Ala—Ala—Leu—Arg—Thr—

Gly—Asp—Asp—Tyr—Val—Ala—Ile—Gly—Ala—Asp—Glu—

Glu—Glu—Leu—Gly—Ser—Gln—Ile—Glu—Glu—Ala—Ile—

Tyr—Gln—Glu—Ile—Arg—Asn—Thr—Asp—Met—Lys—Tyr—

Lys—Asn—Arg—Val—Arg—Ser—Arg—Ile—Ser—Asn—Leu—

Lys—Asp—Ala—Lys—Asn—Pro—Asn—Leu—Arg—Lys—Asn—

Val—Leu—Cys—Gly—Asn—Ile—Pro—Pro—Asp—Leu—Phe—

Ala—Arg—Met—Thr—Ala—Glu—Glu—Met—Ala—Ser—Asp—

Glu—Leu—Lys—Glu—Met—Arg—Lys—Asn—Leu—Thr—Lys—

Glu—Ala—Ile—Arg—Glu—His—Gln—Met—Ala—Lys—Thr—

-continued

Gly—Gly—Thr—Gln—Thr—Asp—Leu—Phe—Thr—Cys—Gly—

Lys—Cys—Lys—Lys—Lys—Asn—Cys—Thr—Tyr—Thr—Gln—

Val—Gln—Thr—Arg—Ser—Ala—Asp—Glu—Pro—Met—Thr—

Thr—Phe—Val—Val—Cys—Asn—Glu—Cys—Gly—Asn—Arg—

Trp—Lys—Phe—Cys or a fragment of the DNA, with a radioisotope to make the cloned DNA into a detectable probe, and dot-blot hybridizing between the probe and variously diluted samples of sample cytoplasmic fraction to quantitatively determine an expression of mRNA. Namely, the diagnostic method of the invention utilizes a finding that the gene expression of transcription factor S-II is different between normal cells and infected cells and that amount thereof on the latter cells shows 10 fold or more value of that on the former cells. When the cloned DNA fragment is employed for the genic diagnosis, the fragment should have a length of about 250 bp or more. The fragment is made into the probe by separating into single-strand DNA and labelled with the radioisotope.

BRIEF DESCRIPTION OF THE DRAWINGS

FIG. 2 shows amino acid sequences determined on peaks I and II in FIG. 1 as well as nucleotide sequences of probes employed for the determination;

FIG. 4 shows a determined nucleotide sequence in the cloned DNA and an amino acid sequence forming an open reading frame therein;

PREFERRED EMBODIMENTS OF THE INVENTION

The invention will now be further explained with reference to Manufacturing Examples, Test Example for determining a structure of cloned DNA obtained by the Manufacturing Example and Diagnostic Example.

EXAMPLE 1

(a) Partial Determination of Amino Acid Sequence for Transcription Factor S-II

The transcription factor S-II (5 nmol) extracted and purified from Ehrlich ascites tumor cells and trypsin treated with tosylphenylalanylchloromethylketone were reacted in 1M-triethylamine/bicarbonate buffer solution and at 37° C. for 12 hours to obtain trypsin-treated fragment of the transcription factor S-II. The trypsin-treated fragment was chromatographed with use of a HPLC system mounted Synchropac RP-P(C-18). The conditions for the chromatography were a linear gradient of 5-60% acetonitrile in 0.05% trifluoroacetate and a flow velocity of 0.5 ml/min. Results are shown in FIG. 1.

Figure 1:
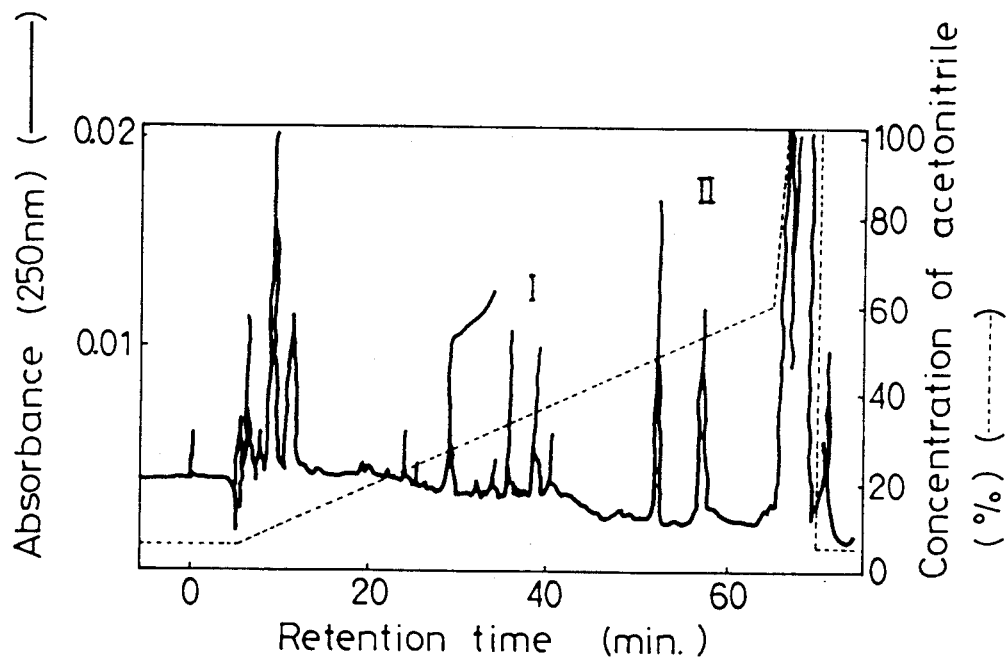
FIG. 1 shows HPLC pattern of the transcription factor S-II which was cleaved with trypsin.

Each of fractions I and II in FIG. 1 was obtained to determine an amino acid sequence with use of a protein sequencer (Type 470A, marketed by Applied Bio-System Corporation). Results are shown in FIG. 2. The Figure also shows nucleotide sequences of DNA employed as probes for determining the amino acid sequence on the peak II.

(b) Synthesis of DNA Complementary to mRNA Corresponding to Amino Acid Sequence for Transcription Factor S-II A mixture of 32 dotriacontamers, each consisting of 14 oligodeoxyribonucleotides of the formula

(A)

which is complementary to mRNA corresponding to

Asp-Asp-Tyr-Val-Ala of 3rd to 7th amino acids from the N-terminus in the amino acid sequence in peak II on the trypsin treated fragment, which amino acid sequence was elucidated by the method as disclosed in said Item (a) and a mixture of 32 dotriacontamers, each consisting of 14 oligodeoxyribonucleotides of the formula

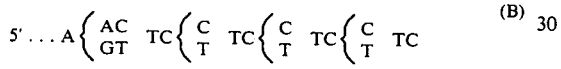
(B)

which is complementary to mRNA corresponding to

Asp-Glu-Glu-Glu-Leu of 11th to 15th amino acids from the N-terminus in the amino acid sequence were synthesized with use of a DNA synthesizer (Gene Assembler, marketed by Pharmacia AB). These synthetic nucleotides cover all possible cases for translating the amino acid sequence.

(c) Cloning

The cloning was carried out in accordance with the method as disclosed by Hanahan, D. et al ["Gene" Vol. 10, pages 63–67 (1980)].

Namely, a cDNA library was prepared with use of poly(A)RNA obtained from Ehrlich ascites tumor cells and a phage vector of λ gt10 and about 30000 transformed cells were taken out from the cDNA library. The transformants were replicated on a nitrocellulose filter. Plaques formed on the filter was fixed thereon with use of 0.5N-NaOH, neutralized to pH 7.5 and dipping the filter in 1.5M-NaCl containing Tris-chloride buffer (pH 7.5) to remove bacterial fragments and the like other than DNA. The filter was then air dried and baked for 2 hours at 80° C. to obtain a testing filter for screening, which carries the DNA of about 30000 transformants.

The screening of the transformants was carried out as follows, in accordance with the method as disclosed by Grunstein, M. et al ["Proc. Natl. Acad. Sci. U.S.A." Vol. 72, pages 3961–3965 (1975)].

Each of the oligodeoxyribonucleotides synthesized by the method as stated in said Item (b) and shown by said formula A was end-labelled at 5'-terminal with an radioisotope of [γ-$^{32}$P]ATP (marketed by Amersham, 5000 Ci/mmol) and T$_4$ polynucleotide kinase (marketed by Toyobo Co., Ltd., Osaka, Japan) to make the oligodeoxyribonucleotides into probes for screening of the transformants. The relative activity of each probe was 1 to $2 \times 10^6$ pm/pmol.

The transformants on the testing filter were screened by a hybridization at 20° C. and with use of the probes (A) and evaluated by an autoradiogram method to find that only 10 transformants among 30000 transformants are positive clones hybridizable with the probes (A).

These positive clones were further screened by another hybridization using the probes (B) which were synthesized as stated in Item (b) and labelled in a manner similar to the above, and judged as above to find that only one transformant is a positive clone hybridizable with the probes (B).

The clone hybridizable with origodeoxyribonucleotides (A) and (B) was analized by an electrophoresis to find that it has a cDNA insert region of about 800 bp. The cDNA insert region was sub-cloned into plasmid pUC8 to obtain a DNA recombinant plasmid which was named as —pS-II-1— (see FIG. 4).

To obtain a clone having longer cDNA insert region, said cDNA insert region having about 800 bp was labelled by a radioisotope of $^{32}$P by nick translation method to make it into a probe. Then, further screening was carried out with use of the probe on about 500000 transformants to obtain 7 positive clones. These positive clones were classified into two groups, one having a cDNA insert region of 2.6 kb and the other having a cDNA insert region of 1.3 kb. Each cDNA insert region was sub-cloned to plasmid pBSM13 to obtain a DNA recombinant plasmid which was named as —pSII-2— and —pSII-3—, respectively (see FIG. 4).

Since each cDNA is double-strand and its nucleotide sequence has been elucidated as disclosed in the Test Example given later, it may be made into a fragment having various lengths in cDNA insert region, with use of a suitable restriction enzyme and a suitable synthetic DNA. These double-strand DNA or its fragments can be ligated into various plasmids, in accordance with conventional techniques, for instance by taking out a plasmid from E. coli, purifying same, treating the plasmid with a restriction enzyme to cleave the plasmid at a specified nucleotide position inherent to the restriction enzyme, and ligating with a DNA ligase the cloned DNA or its fragment to the cleavages of the cleaved plasmid to re-construct a plasmid with recombinant DNA. A microorganism or eukaryotic cell can be transformed with such DNA recombinant plasmid in a conventional manner and cultivated to produce the transcription factor S-II or other specific biologically active substances, in a large amount.

TEST EXAMPLE (Determination of nucleotide sequence for cDNA including transcription factor S-II clone and amino acid sequence of the transcription factor S-II region)

A nucleotide sequence of cDNA clone encoding a transcription factor S-II was determined in accordance with the dideoxy method as disclosed by Sanger et al ["Proc. Natl. Acad. Sci. U.S.A." Vol. 74, pages 5463–5467 (1977)] and with use of the DNA recombinant plasmids, pS-II-1, pS-II-2 and pS-II-3 as disclosed in Item (c) of the Manufacturing Example 1.

Figure 3:
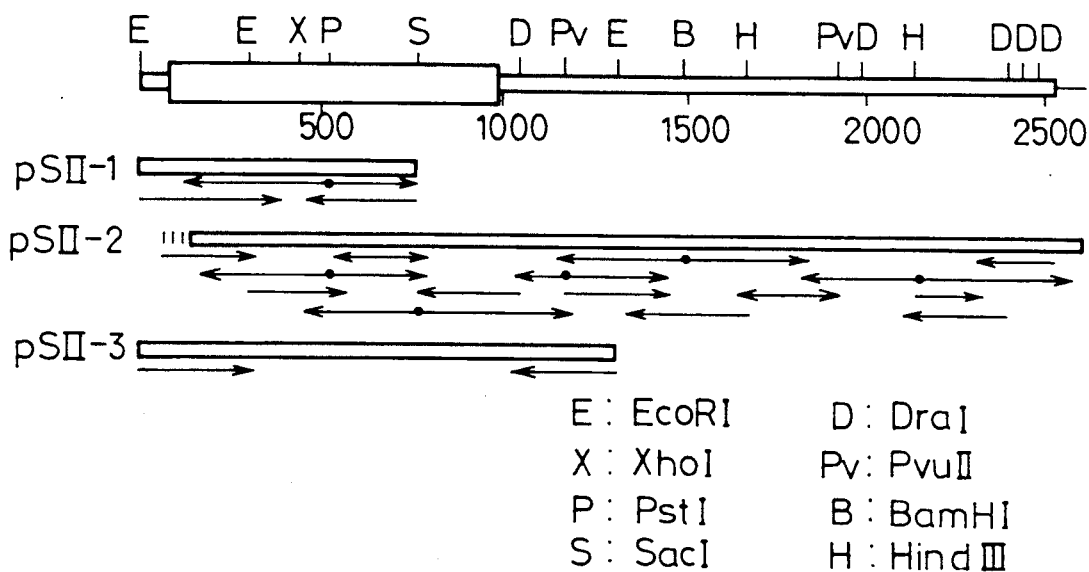
FIG. 3 shows a cloned DNA region including transcription factor S-II, restriction enzymes employed for determining nucleotide sequence in the region and a strategy for the determination of nucleotide sequence.

In FIG. 3, there are shown restriction enzymes employed for determining the nucleotide sequence and strategy for sequencing the cloned cDNA. In the Figure, symbols at uppermost portion are names of the selected restriction enzymes, in which X is XhoI, P PstI, S SacI, D DraI, Pv PvuII, B BamHI and H HindIII, respectively. A boxed region shows the region encoding the transcription factor S-II and upper and down stream regions are nontranslated flanking ones. The numerals at the middle portion are the nucleotide number. In the lowermost portion, horizontal arrows show a direction and range of the nucleotide sequence to be determined by the respective restriction enzyme.

Resulting nucleotide sequence of the transcription factor S-II clone is shown in FIG. 4 together with the corresponding amino acid sequence. In this Figure, numerals given at upper side of the nucleotide sequence are number of nucleotides as in FIG. 3, numerals given at right side of the amino acid sequence are the number of amino acid residues in the transcription factor S-II region, and the region boxed with a solid line shows that having the amino acid sequence overlaps with a part of the amino acid sequence for transcription factor S-II, which was previously determined by the present inventor. The transcription factor S-II region lies as a long open reading frame beginning from the initiation codon of ATG and ending with the termination codon of TGA and includes nucleotide sequence encoding 301 amino acids. Near the 3'-end region, there is a nucleotide sequence AATAA (positions in upper stream of poly(A) sequence by 17 and 106 nucleotide residues) which is usually found in upper stream of poly(A) sequence in eukaryotic mRNA.

EXAMPLE 2

(Preparation of plasmid containing a cDNA clone encoding transcription factor S-II)

Figure 5:
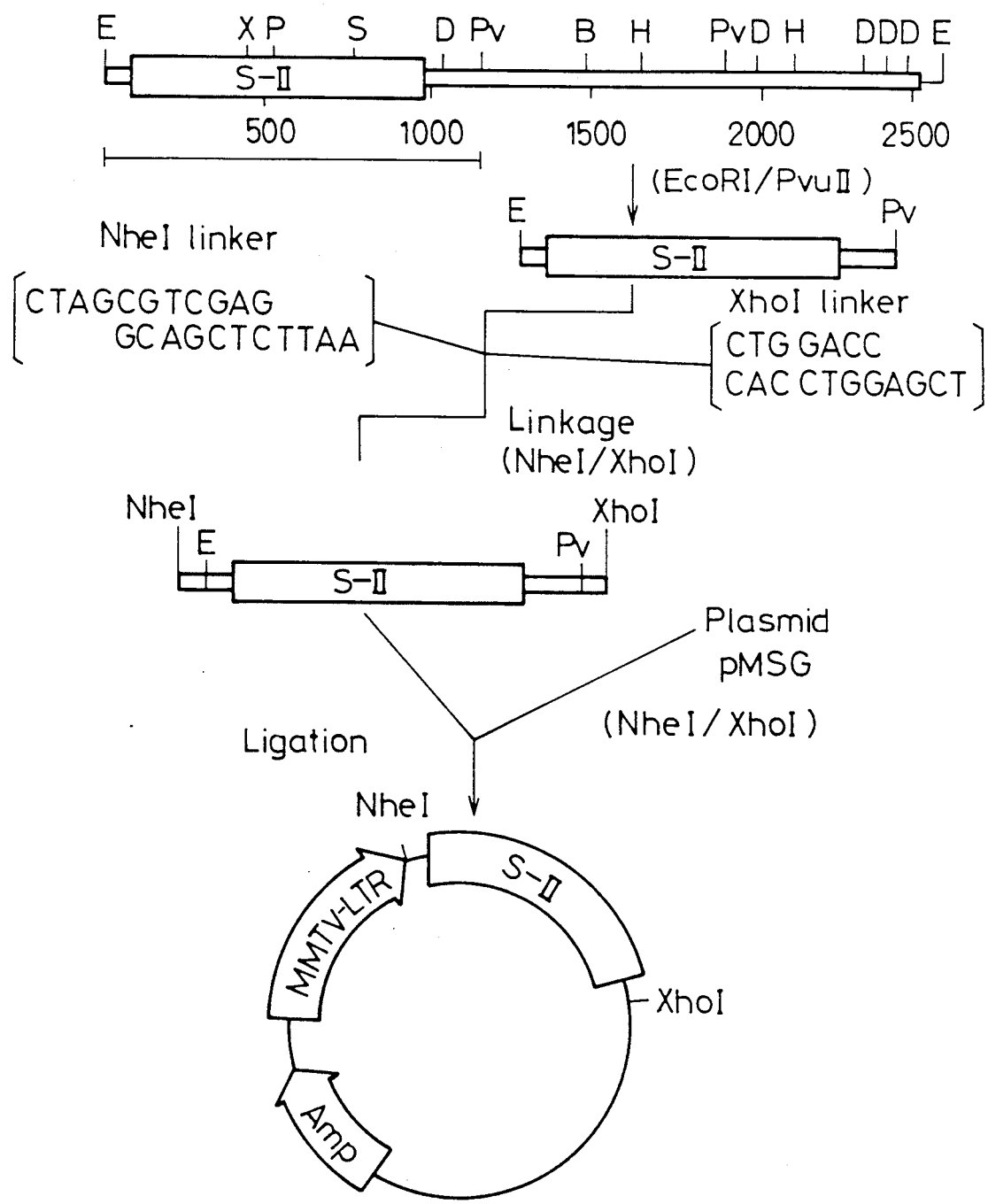
FIG. 5 illustrates steps for preparing a plasmid, wherein the transcription factor S-II is inserted.

This embodiment will be explained with reference to the drawings and more particularly FIG. 5. First, the long DNA clone shown in FIGS. 3 and 4 was treated with restriction enzymes of EcoRI and PvuII to prepare a fragment of about 1100 bp. On the other hand, NheI and XhoI linkers as shown in FIG. 5 were prepared with use of a DNA synthesizer marketed by Pharmacia AB. These linkers were ligated to the EcoRI and PvuII sites, respectively.

A commercially available plasmid (pMSG) was treated with restriction enzymes of NheI and XhoI and said DNA encoding transcription factor S-II with the linkers was ligated with a DNA ligase to the cleavages of the plasmid to re-construct a desired plasmid. As shown at the last portion in FIG. 5, the resulting plasmid has the DNA clone of transcription factor S-II downstream of a powerful promoter (MMTV-LTR) which is long terminal repeat of mouse mammary tumor virus. The plasmid with such recombinant DNA can transform *E. coli* or the like, in a conventional manner, to produce the transcription factor S-II in a large amount.

DIAGNOSTIC TEST (Diagnosis of AIDS with use of cDNA clone for transcription factor S-II)

a) Preparation of probe

The long DNA clone (single-strand DNA) for the transcriptional accelerator S-II and as shown in FIGS. 3 to 5 was treated with restriction enzymes EcoRI and PstI to prepare a fragment of about 600 bp. The fragment was labelled with radioisotope of $^{32}P$ by the nick translation method to make it into a probe.

b) Preparation of test samples

Cell strains of MoLT-4/III and Molt-4 were selected for the test, the former strain a source of HIV and the latter producing almost no HIV. Each of the strains was drawn into an Eppendorf pipette ($10^6$ cells) and washed with 1 ml of phosphate buffer solution. In 45 μl of ice-cooled 10 mM-Tris chloride buffer containing 1 mM-EDTA, the cells were suspended and 5 μl of Nonidet P-40 (surface active agent marketed by Shell Chemicals Inc.) were added twice to the suspension and placed in ice-bath for breaking the cells. The resulting solution was centrifuged (15000×g, 2.5 min.) to obtain a supernatant. The supernatant (50 μl) was collected into an Eppendorf tube, in which 30 μl of 20×NaCl/Cit (0.15M-NaCl/0.015M-sodium citrate) and 20 μl of 37(W/W) % formaldehyde solution had been previously added, to incubate at 60° C. for 15 minutes, so as to prepare an original sample solution. Preservation of the original sample solution shall be made at a temperature of −70° C.

c) Preparation of testing filters

Each of original sample solutions was taken up in 20 μl, which was diluted with 15×NaCl/Cit in a serial system to prepare various test sample solutions, each having volume of 150 μl. Each diluted test sample solution was applied as 4 mm spots on a nitrocellulose sheet set on a 96 hole minifold marketed by Schleicher & Schuell GmbH and then the nitrocellulose sheet was baked at 80° C. for 3 hours to prepare a desired test filter.

d) Operation, results and consideration

A dot-blot hybridization was carried out with use of the probe stated in said Item a) and the test filter described therein item c) and the intensity of each spot was checked with an autoradiograph scanning to measure an expression of mRNA of transcription factor S-II.

Figure 6:
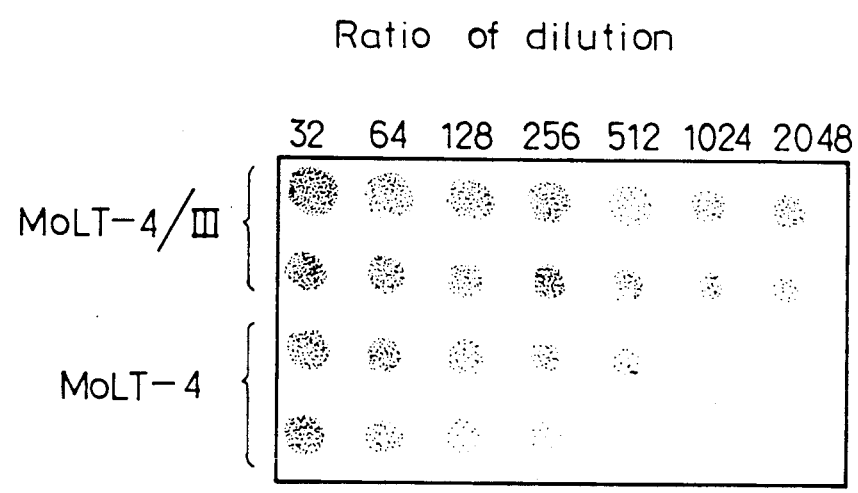
FIG. 6 shows results of diagnosis on AIDS, which was carried out by dot-blot hybridization method with use of the cloned DNA according to the invention.

Results are shown in FIG. 6. As apparently seen therefrom, a spot will not be recognized on the samples diluted 512 fold or more, in the MoLT-4 cells which discharge almost no AIDS virus. In the MoLT-4/III cells discharging HIV in a higher ratio, on the contrary thereto, a spot can be recognized, even when the sample was diluted by 2048 folds.

Therefore, if the operation as above will be carried out by selecting blood or the like cytoplasmic fraction, as an original sample, a diagnosis on AIDS is possible. Further, an accuracy of the diagnosis on AIDS can remarkably be increased, when both of this genetic assay and a conventional antibody assay are carried out in combination.

What is claimed is:

1. A method for the identification of a gene encoding transcription factor S-II comprising probing a cDNA library made from Ehrlich ascites cells with two sets of synthetic oligonucleotides, one set comprising all possible codon combinations for amino acid 3 to amino acid 7 of transcription factor S-II and one set comprising all possible codon combinations for amino acid 11 to amino acid 15 of transcription factor S-II.

2. A cloned single- or complementary, double-stranded DNA having the following sequence, 5' to 3' of

5'... ATG GAG GAC GAG GTG GTT CGC ATT GCC

AAG AAG ATG GAC AAA ATG GTG CAG AAA AAG

-continued

AAT GCG GCT GGC GCA TTG GAT TTG CTG AAA GAG

CTT AAG AAT ATT CCC ATG ACC CTA GAA TTG CTA

CAG TCC ACA AGA ATT GGA ATG TCT GTC AAT GCC

CTT CGC AAG CAC AGC ACA GAT GAA GAA GTC ACC

TCT CTA GCC AAG TCT CTC ATC AAA TCC TGG AAA

AAA TTA TTA GAT GGA CCA TCA ACT GAT AAA GAC

CCT GAA GAA AAG AAA AAA GAG CCT GCA ATT TCA

TCA CAG AAT AGC CCT GAA GCA AGA GAA GAA

AGT AGT TCC AGC AGC AAT GTA AGC AGC AGA

AAG GAT GAC ACA AAT GCT CGA GAT ACA TAT GTT

TCA TCT TTT CCT CGC GCA CCA AGC ACT TCT GAT

TCT GTG CGA TTA AAA TGT AGG GAC ATG CTT GCT

GCA GCT CTT CGC ACA GGA GAT GAT TAT GTT GCA

ATT GGA GCT GAT GAA GAA GAA CTG GGA TCT

CAG ATT GAG GAA GCT ATA TAT CAA GAA ATA AGG

AAT ACA GAC ATG AAA TAC AAA AAC AGA GTA CGA

ACT AGG ATA TCA AAT CTT AAA GAT GCA AAG AAT

CCA AAT TTA AGG AAA AAT GTG CTG TGT GGG AAT

ATT CCT CCT GAT CTA TTT GCT AGA ATG ACA GCA

GAG GAA ATG GCT AGT GAT GAG CTC AAA GAG

ATG AGG AAA AAC CTG ACC AAA GAA GCC ATC

AGG GAG CAT CAG ATG GCC AAG ACT GGT GGG

ACC CAG ACT GAC TTG TTC ACT TGT GGC AAA TGT

AAA AAG AAG AAC TGC ACT TAT ACA CAG GTG CAA

ACT CGT AGT GCT GAT GAA CCA ATG ACA ACA TTT

GTT GTA TGT AAT GAA TGT GGA AAT CGG TGG AAG

TCC TGT ... 3' encoding an amino acid sequence for transcription factor S-II.

3. A cloned single-strand DNA or double-strand DNA, wherein said DNA encodes an amino acid sequence of Met—Glu—Asp—Glu—Val—Val—Arg—Ile—Ala—Lys—Lys—

Met—Asp—Lys—Met—Val—Gln—Lys—Lys—Asn—Ala—Gly—

Ala—Ala—Leu—Asp—Leu—Leu—Lys—Glu—Leu—Lys—Asn—

Ile—Pro—Met—Thr—Leu—Glu—Leu—Leu—Gln—Ser—Thr—

Arg—Ile—Gly—Met—Ser—Val—Asn—Ala—Leu—Arg—Lys—

Gln—Ser—Thr—Asp—Glu—Glu—Val—Thr—Ser—Leu—Ala—

Lys—Ser—Leu—Ile—Lys—Ser—Trp—Lys—Lys—Leu—Leu—

Asp—Gly—Pro—Ser—Thr—Asp—Lys—Asp—Pro—Glu—Glu—

Lys—Lys—Lys—Glu—Pro—Ala—Ile—Ser—Ser—Gln—Asn—

-continued

Ser—Pro—Glu—Ala—Arg—Glu—Glu—Ser—Ser—Ser—

Ser—Asn—Val—Ser—Ser—Arg—Lys—Asp—Glu—Thr—Asn—

Ala—Arg—Asp—Thr—Tyr—Val—Ser—Ser—Phe—Pro—Arg—

Ala—Pro—Ser—Thr—Ser—Asp—Ser—Val—Arg—Leu—Lys—

Cys—Arg—Glu—Met—Leu—Ala—Ala—Ala—Leu—Arg—Thr—

Gly—Asp—Asp—Tyr—Val—Ala—Ile—Gly—Ala—Asp—Glu—

Glu—Glu—Leu—Gly—Ser—Gln—Ile—Glu—Glu—Ala—Ile—

Tyr—Gln—Glu—Ile—Arg—Asn—Thr—Asp—Met—Lys—Tyr—

Lys—Asn—Arg—Val—Arg—Ser—Arg—Ile—Ser—Asn—Leu—

Lys—Asp—Ala—Lys—Asn—Pro—Asn—Leu—Arg—Lys—Asn—

Val—Leu—Cys—Gly—Asn—Ile—Pro—Pro—Asp—Leu—Phe—

Ala—Arg—Met—Thr—Ala—Glu—Glu—Met—Ala—Ser—Asp—

Glu—Leu—Lys—Glu—Met—Arg—Lys—Asn—Leu—Thr—Lys—

Glu—Ala—Ile—Arg—Glu—His—Gln—Met—Ala—Lys—Thr—

Gly—Gly—Thr—Gln—Thr—Asp—Leu—Phe—Thr—Cys—Gly—

Lys—Cys—Lys—Lys—Asn—Cys—Thr—Tyr—Thr—Gln—

Val—Gln—Thr—Arg—Ser—Ala—Asp—Glu—Pro—Met—Thr—

Thr—Phe—Val—Val—Cys—Asn—Glu—Cys—Gly—Asn—Arg—

Trp—Lys—Phe—Cys

4. A plasmid which incorporates a double-strand DNA consisting of a cloned single-strand DNA comprising about 900 nucleotides encoding an amino acid sequence for transcription factor S-II according to claim 3, and its complementary strand.

5. A single-stranded DNA having a nucleotide sequence comprising:

AATTCGGACAGCGGACGGGAAGCGAGAGAAGCTGCG

CGGACGTTGGACAAGCCGCGAACGCGCTGGCCGAGG

CCTTCCGGAGCCATGGAGGACGAGGTGGTTCGCATTG

CCAAGAAGATGGACAAAATGGTGCAGAAAAAGAATG

CGGCTGGCGCATTGGATTTGCTGAAAGAGCTTAAGAA

TATTCCCATGACCCTAGAATTGCTACAGTCCACAAGAA

TTGGAATGTCTGTCAATGCCCTTCGCAAGCAGAGCAC

AGATGAAGAAGTCACCTCTCTAGCCAAGTCTCTCATCA

AATCCTGGAAAAAATTATTAGATGGACCATCAACTGA

TAAAGACCCTGAAGAAAGAAAAAAGAGCCTGCAATT

TCATCACAGAATAGCCCTGAAGCAAGAGAAGAAAGTA

GTTCCAGCAGCAATGTAAGCAGCAGAAAGGATGAGA

CAAATGCTCGAGATACATATGTTTCATCTTTTCCTCGC

GCACCAAGCACTTCTGATTCTGTGCGATTAAAATGTA

GGGAGATGCTTGCTGCA.

* * * * *